US012648909B1

(12) United States Patent
Omran et al.

(10) Patent No.: US 12,648,909 B1
(45) Date of Patent: Jun. 9, 2026

(54) METHOD OF TREATING CANCER CELLS USING CaMoO₄/CaSiO₃/g-C₃N₄ CRYSTALLINE NANOCOMPOSITE MATERIAL

(71) Applicant: IMAM MOHAMMAD IBN SAUD ISLAMIC UNIVERSITY, Riyadh (SA)

(72) Inventors: Mohamed Khairy Abdel Fattah Omran, Riyadh (SA); Babiker Yagoub Elhadi Abdulkhair, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 19/269,182

(22) Filed: Jul. 15, 2025

(51) Int. Cl.
| | |
|---|---|
| *A61P 35/00* | (2006.01) |
| *A61K 9/14* | (2006.01) |
| *A61K 33/06* | (2006.01) |
| *A61K 33/24* | (2019.01) |

(52) U.S. Cl.
CPC .............. *A61K 9/143* (2013.01); *A61K 33/06* (2013.01); *A61K 33/24* (2013.01); *A61P 35/00* (2018.01)

(58) Field of Classification Search
CPC ........ A61K 9/141; A61K 9/143; A61K 9/148; A61P 35/00; A61P 35/02; A61P 35/04
See application file for complete search history.

(56) References Cited

FOREIGN PATENT DOCUMENTS

| | | |
|---|---|---|
| CN | 115515900 A | 12/2022 |
| CN | 118807812 A | 10/2024 |
| KR | 10-2022-0021747 A | 2/2022 |

OTHER PUBLICATIONS

Santiago et al (Enhanced photocatalytic activity of CaMoO4/g-C3N4 composites obtained via chemistry synthesis, Materials Research Bulletin, 146, 2022 (Year: 2022).*
(Graphitic carbon nitride as a novel anticancer agent: potential mechanisms and efficacy in prostate and glioblastoma treatment, Biomater. Sci., 12, 5547-5561, 2024 (Year: 2024).*
Different effects of a novel CaO—MgO—SiO2-based multiphase glass-ceramic on cell behaviors of normal and cancer cells in vitro, Controls and Surfaces Biointerfaces 116, 1-8, 2014 (Year: 2014).*
Selvaganapathy Ganesan, et al., "Sulfur-doped graphitic C3N4 decorated on cauliflower-like CaMoO4: An efficient electrocatalyst for electrochemical detection of carcinogenic organic pollutant (metol)", Chemosphere, vol. 369, Dec. 2024, 143815, 9 Pages.
Guangyuan Yao, et al., "Synthesis and enhanced visible-light photocatalytic activity of wollastonite/g-C3N4 composite", Materials Research Bulletin, vol. 86, Feb. 2017, pp. 186-193, 8 pages.
Anderson A.G. Santiago, et al., "Enhanced photocatalytic activity of CaMoO4/g-C3N4 composites obtained via sonochemistry synthesis", Materials Research Bulletin, vol. 146, Feb. 2022, 11621, 9 pages.

* cited by examiner

*Primary Examiner* — Micah Paul Young
(74) *Attorney, Agent, or Firm* — Oblon, McClelland, Maier & Neustadt, L.L.P.

(57) ABSTRACT

A method of treating cancer cells includes incubating the cancer cells with a particulate crystalline nanocomposite and killing at least 60% of the cancer cells. The particulate crystalline nanocomposite includes a tetragonal CaMoO₄ crystalline phase, a CaSiO₃ crystalline phase, and a graphitic-C₃N₄ crystalline phase, where at least a fraction of the graphitic-C₃N₄ is in the form of mesoporous nanosheets.

17 Claims, 6 Drawing Sheets

METHOD OF TREATING CANCER CELLS USING CaMoO4/CaSiO3/g-C3N4 CRYSTALLINE NANOCOMPOSITE MATERIAL

BACKGROUND

Technical Field

The present disclosure is directed to a nanocomposite material and, more particularly, a method of treating cancer using a particulate crystalline nanocomposite including a tetragonal $CaMoO_4$ crystalline phase, a $CaSiO_3$ crystalline phase, and a graphitic-$C_3N_4$ crystalline phase.

Description of Related Art

The 'background' description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Cancer is the leading cause of death and disability in the world, and due to its complicated pathological process, treatment of cancer remains a substantial challenge. Numerous treatment methods have been developed over the decades, among which the conventional chemotherapy is the major treatment method despite many disadvantages including cytotoxicity, low therapeutic indices, low bioavailability, insolubility, high dose requirements, non-specific targeting, and the development of multiple drug resistance. However, patients have been observed to develop resistance towards cancer treatment, including overexpression of drug efflux transporters, anoxic conditions, and abnormal apoptotic pathways, which results in inefficiency in the course of treatment. Nanomaterials (NMs) have been proposed to address the issue arose from cancer treatment resistance, and have gained much interest as potential anticancer agents ever since. Due to their advantages in the size, shape, and surface optimization, NMs may improve targeting efficiency and circulation time, which in turn increases the targeting potential of anticancer cargos. Further, NMs may boost therapeutic efficacy by controlled release by targeting cargos to cancer sites through encapsulation or coupling with ligands. In cancer treatment, NMs are often used to target cancer cells, tumor microenvironment, and immune system primarily through stimuli-responsive targeting or by modifying their surfaces with targeting ligands like transferrin, integrins, sugar, folic acid, and antibodies to improve tissue targeting recognition and internalization.

Although several nanomaterials have been used in the past for cancer treatment, there still exists a need to develop nanomaterials with improved selectivity and cytotoxic activity against cancer cells.

SUMMARY

In an exemplary embodiment, a method of treating cancer cells is described. The method includes incubating a plurality of cancer cells with a particulate crystalline nanocomposite in an amount sufficient to induce apoptosis or kill at least 60% of the cancer cells. The particulate crystalline nanocomposite includes a tetragonal $CaMoO_4$ crystalline phase, a $CaSiO_3$ crystalline phase, and a graphitic-$C_3N_4$ crystalline phase having at least a fraction in the form of mesoporous nanosheets. The cancer cells are breast cancer cells or liver cancer cells.

In some embodiments, a ratio by weight of $CaMoO_4$ to $CaSiO_3$ to graphitic-$C_3N_4$ in the particulate crystalline nanocomposite is about (0.8-1.2):(0.8-1.2):(0.8-1.2).

In some embodiments, at least a fraction of the $CaMoO_4$ and at least a fraction of the $CaSiO_3$ of the particulate crystalline nanocomposite are in the form of substantially spherical particles.

In some embodiments, at least 50 wt. % of the $CaMoO_4$ of the particulate crystalline nanocomposite is in the form of substantially spherical particles based on a total weight of the $CaMoO_4$, and at least 50 wt. % of the $CaSiO_3$ of the particulate crystalline nanocomposite is in the form of substantially spherical particles based on a total weight of the $CaSiO_3$.

In some embodiments, the substantially spherical particles have an average particle size of from about 5 to about 20 nm.

In some embodiments, at least 50 wt. % of the graphitic-$C_3N_4$ is in the form of mesoporous nanosheets, based on a total weight of the graphitic-$C_3N_4$.

In some embodiments, at least 80 wt. % of the graphitic-$C_3N_4$ is in the form of mesoporous nanosheets, based on a total weight of the graphitic-$C_3N_4$.

In some embodiments, the particulate crystalline nanocomposite has a monomodal pore size distribution.

In some embodiments, the particulate crystalline nanocomposite has an average pore diameter of from about 15 to about 25 nm.

In some embodiments, the particulate crystalline nanocomposite has an average pore diameter of from about 15 to about 20 nm.

In some embodiments, the particulate crystalline nanocomposite has a Brunauer-Emmett-Teller (BET) surface area of from about 60 to about 100 $m^2/g$.

In some embodiments, the particulate crystalline nanocomposite has a BET surface area of from about 70 to about 90 $m^2/g$.

In some embodiments, the particulate crystalline nanocomposite has a pore volume of from about 0.1 to about 0.3 $cm^3/g$.

In some embodiments, the cancer cells are of estrogen receptor positive breast cancer.

In some embodiments, the cancer cells are of human breast carcinoma.

In some embodiments, the cancer cells are obtained from hepatocellular carcinoma (HCC), cholangiocarcinoma, angiosarcoma, or fibrolamellar hepatocellular carcinoma.

In some embodiments, the cancer cells are of Human Hepatocellular Carcinoma.

In another exemplary embodiment, a pharmaceutical composition is described. The pharmaceutical composition includes at least one pharmaceutically acceptable excipient and a particulate crystalline nanocomposite including a tetragonal $CaMoO_4$ crystalline phase, a $CaSiO_3$ crystalline phase, and a graphitic-$C_3N_4$ crystalline phase. At least a fraction of the graphitic-$C_3N_4$ is in the form of mesoporous nanosheets.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained

Figure 1:
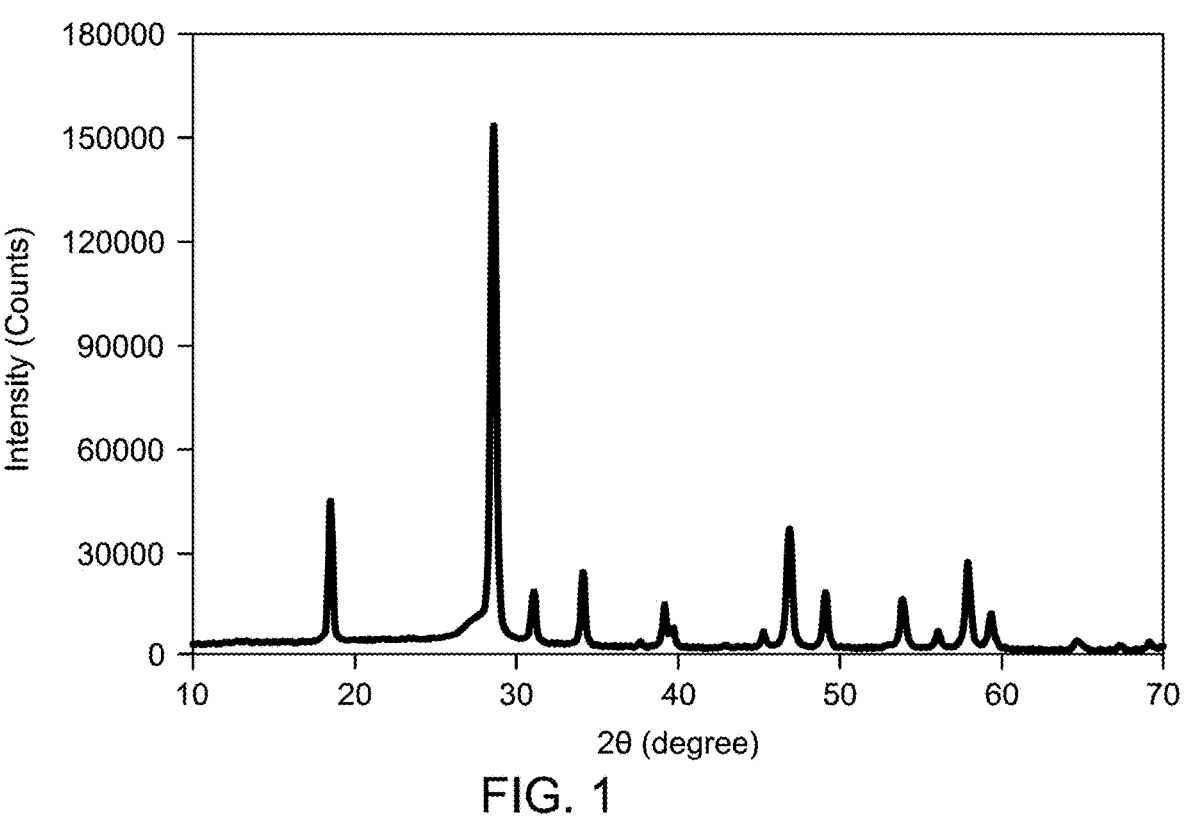

3 as the same becomes better understood by reference to the following detailed description when considered in connection with the accompanying drawings, wherein:

FIG. 1 shows an X-ray diffractogram (XRD) spectrum of a particulate crystalline nanocomposite comprising $CaMoO_4$, $CaSiO_3$ and g-$C_3N_4$ ($CaMoO_4$/$CaSiO_3$/g-$C_3N_4$ composite), according to certain embodiments.

Figure 2A:
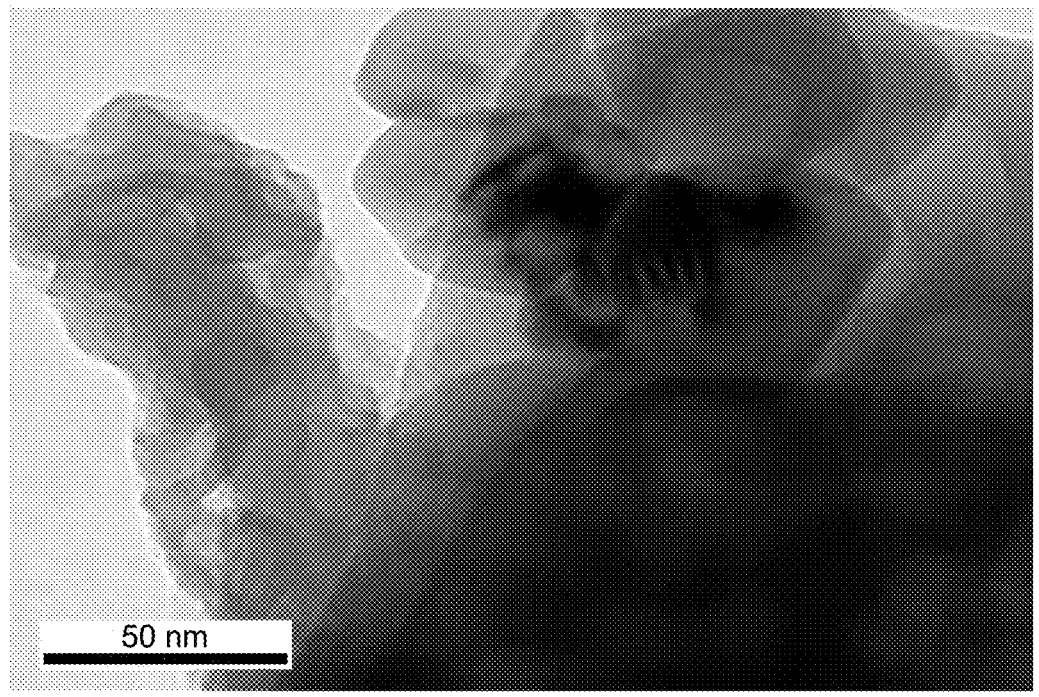

FIG. 2A is a transmission electron microscopy (TEM) image of the $CaMoO_4$/$CaSiO_3$/g-$C_3N_4$ nanocomposite with a scale bar of 50 nanometers (nm), according to certain embodiments.

Figure 2B:
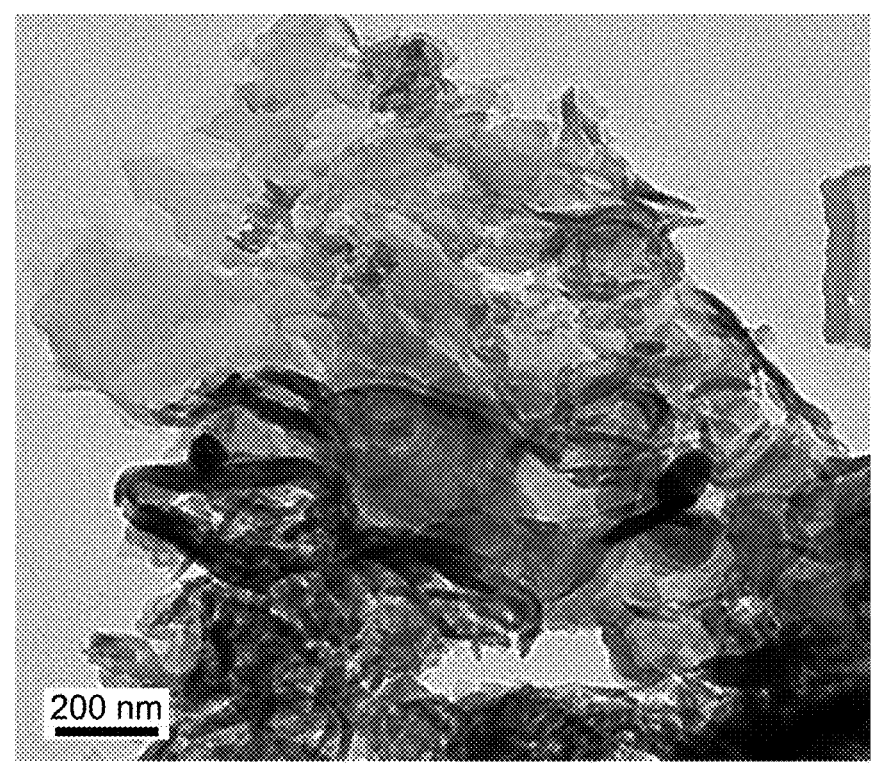

FIG. 2B is a TEM image of the $CaMoO_4$/$CaSiO_3$/g-$C_3N_4$ nanocomposite with a scale bar of 200 nm, according to certain embodiments.

Figure 2C:
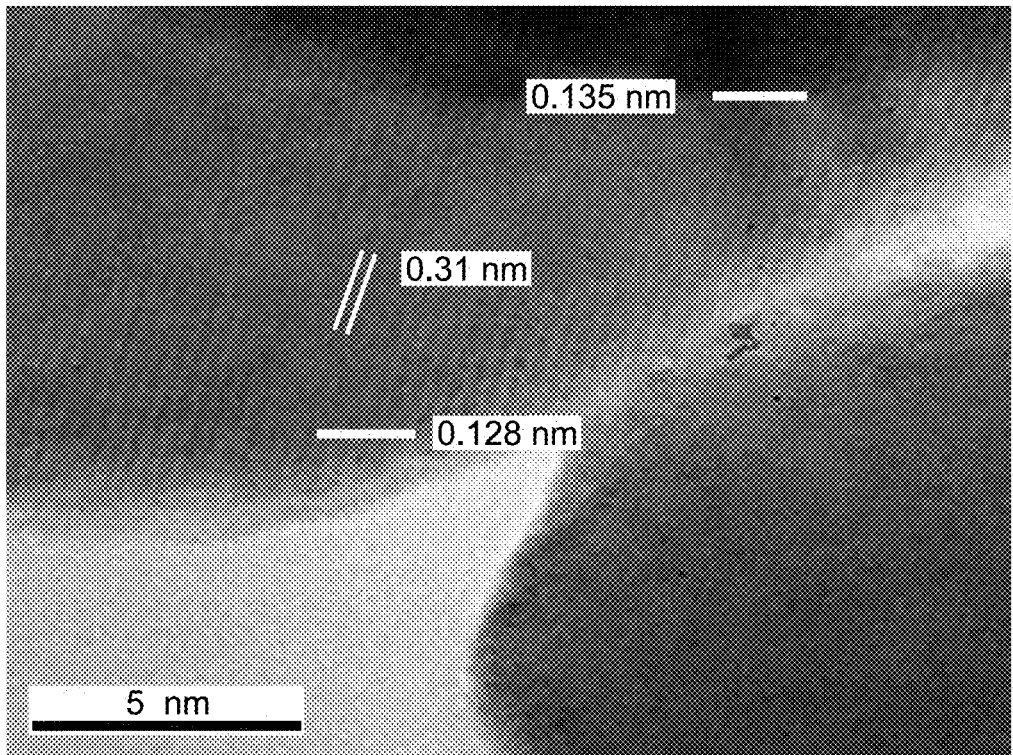

FIG. 2C is a high-resolution transmission electron microscope (HR-TEM) image of the $CaMoO_4$/$CaSiO_3$/g-$C_3N_4$ nanocomposite with a scale bar of 5 nm, according to certain embodiments.

Figure 2D:
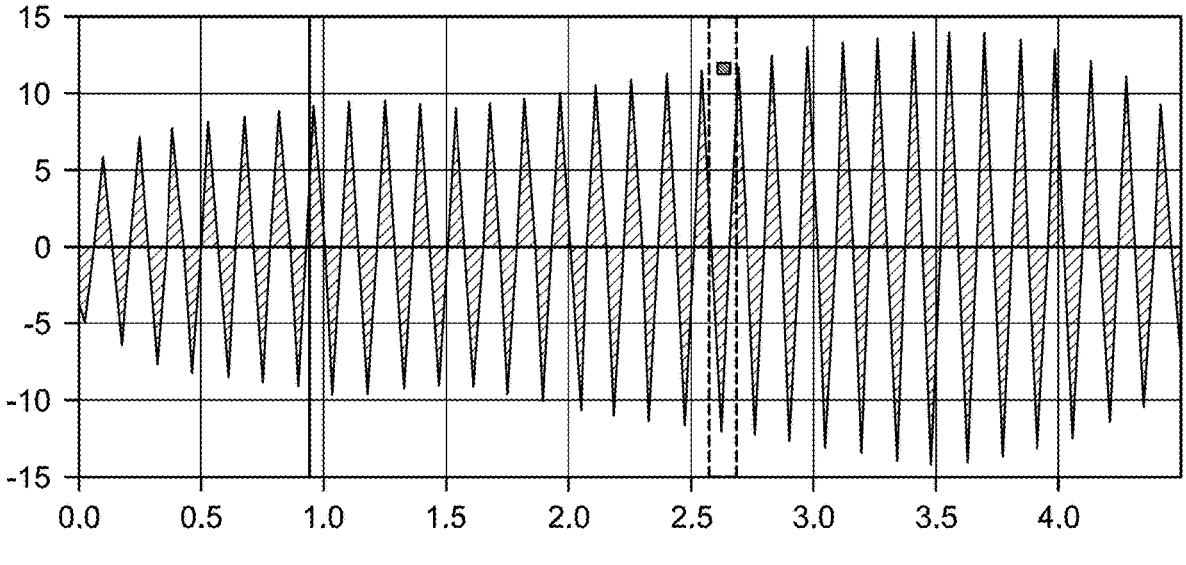

FIG. 2D is a fast Fourier transform (FFT) spectrum of the $CaMoO_4$/$CaSiO_3$/g-$C_3N_4$ nanocomposite, according to certain embodiments.

Figure 2E:
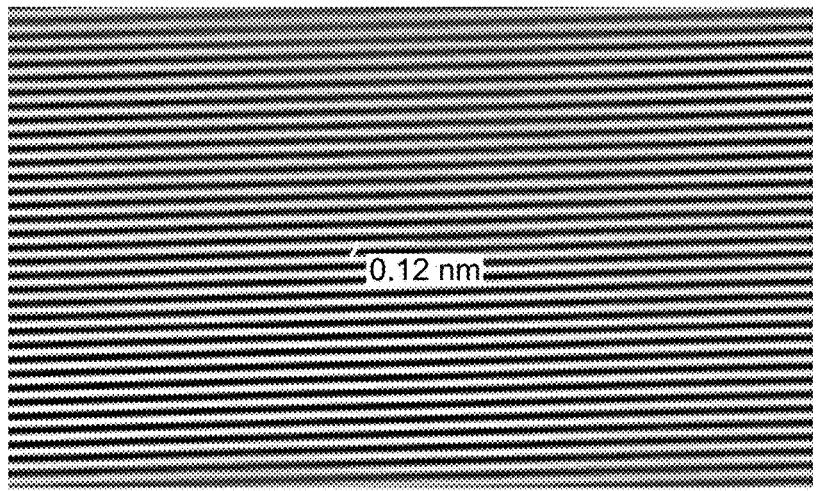

FIG. 2E is an inverse fast Fourier transform (IFFT) spectrum of the $CaMoO_4$/$CaSiO_3$/g-$C_3N_4$ nanocomposite, according to certain embodiments.

Figure 2F:
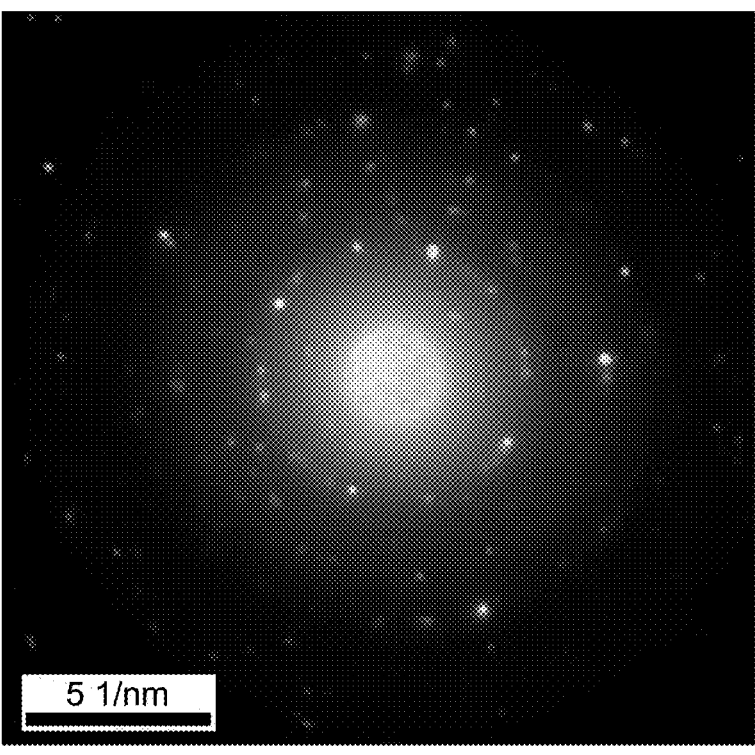

FIG. 2F is a selected area electron diffraction (SAED) pattern of the $CaMoO_4$/$CaSiO_3$/g-$C_3N_4$ nanocomposite, according to certain embodiments.

Figure 3A:
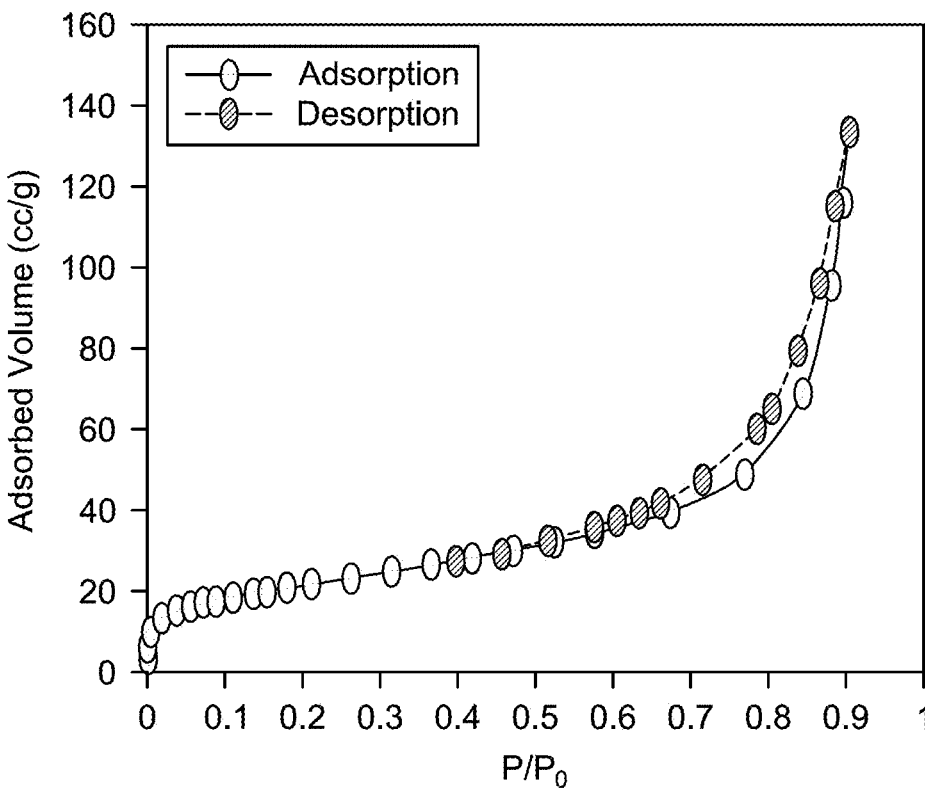

FIG. 3A is a graph depicting a nitrogen adsorption-desorption isotherm of the $CaMoO_4$/$CaSiO_3$/g-$C_3N_4$ nanocomposite, according to certain embodiments.

Figure 3B:
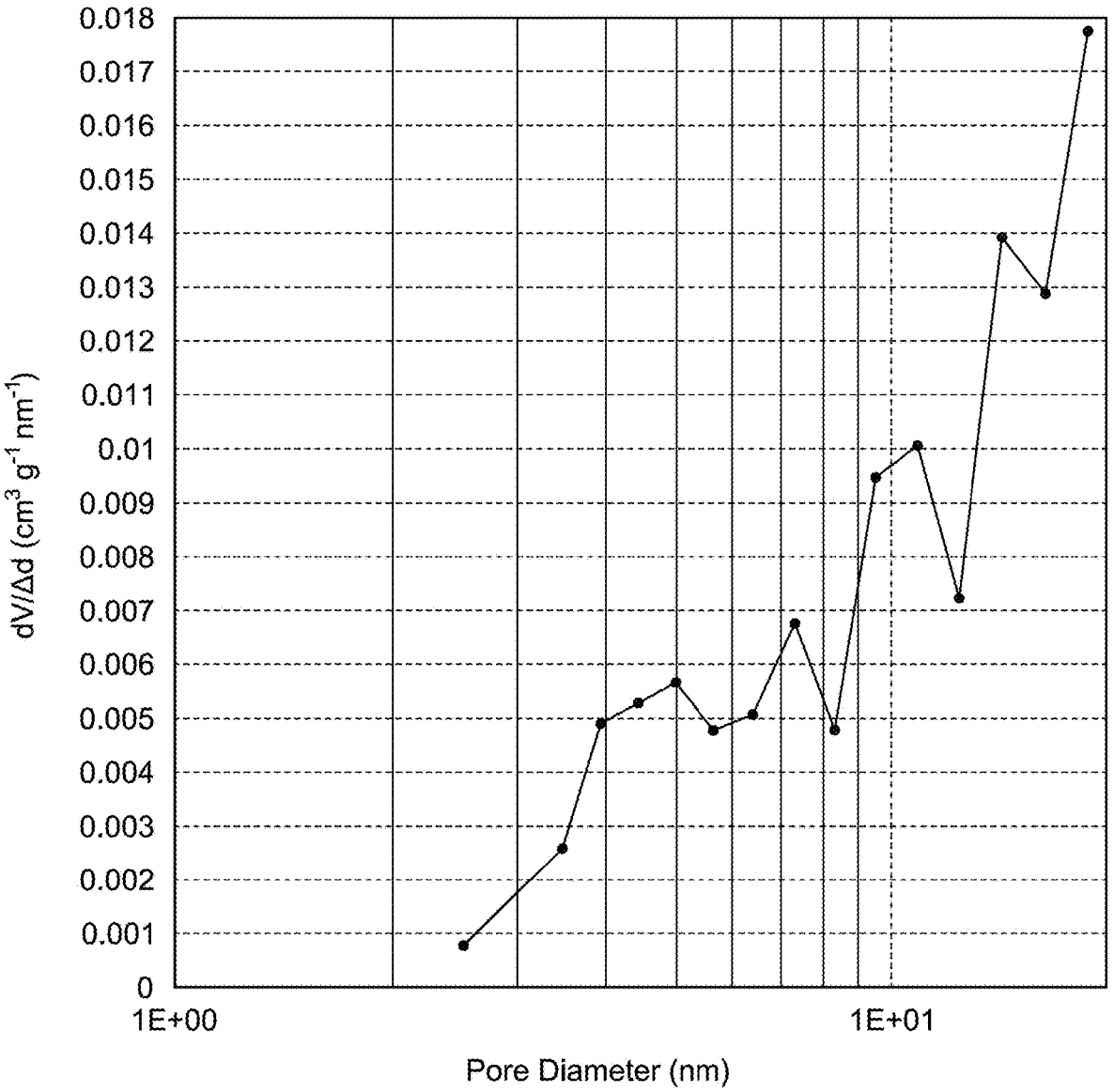

FIG. 3B is a graph depicting a pore size distribution of the $CaMoO_4$/$CaSiO_3$/g-$C_3N_4$ nanocomposite, according to certain embodiments.

Figure 4:
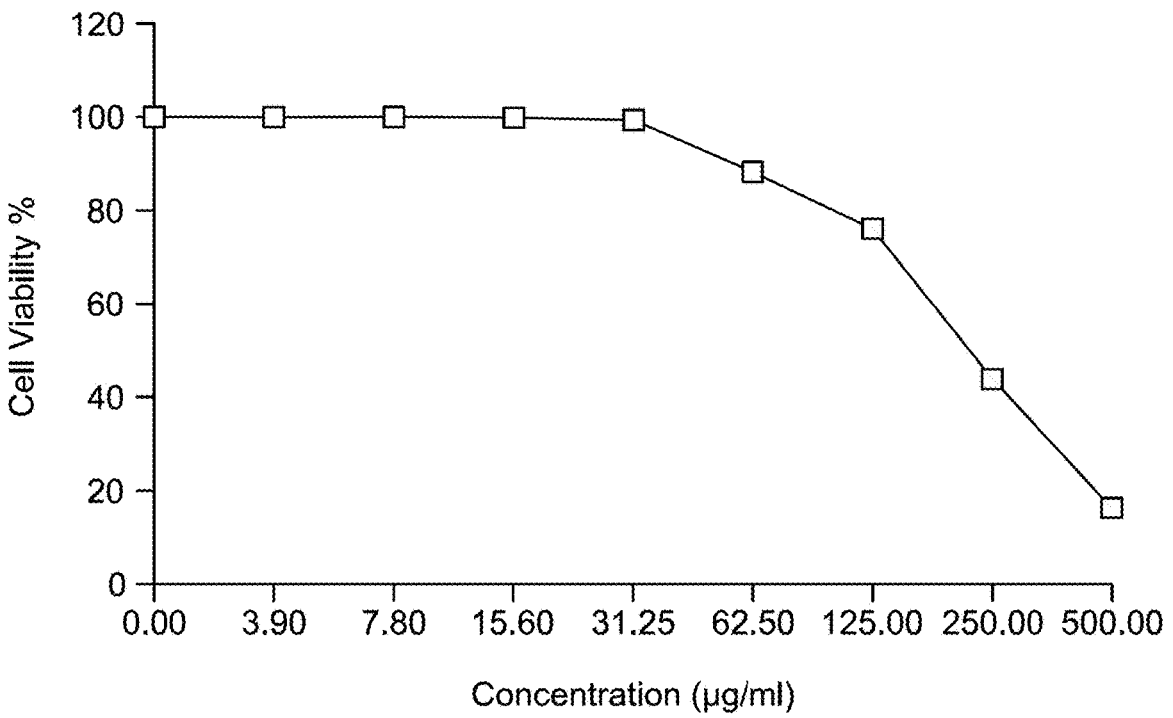

FIG. 4 is a graph depicting an inhibitory activity of the $CaMoO_4$/$CaSiO_3$/g-$C_3N_4$ nanocomposite against MCF-7 cells, according to certain embodiments.

Figure 5:
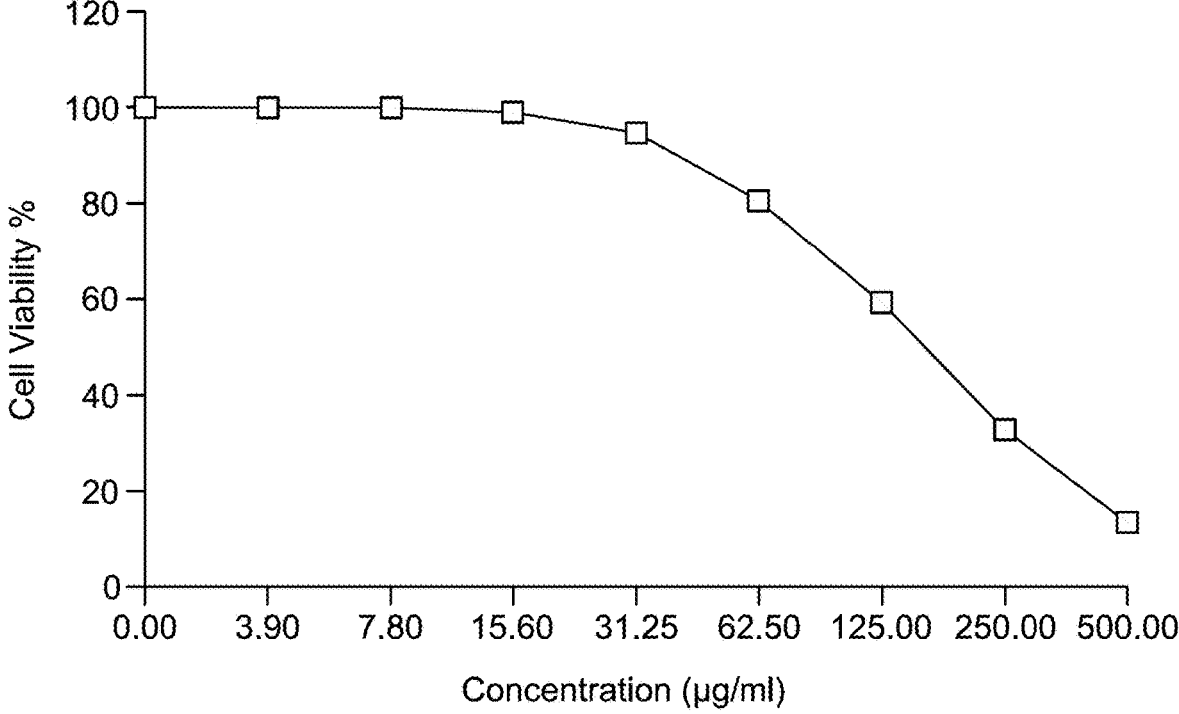

FIG. 5 is a graph depicting an inhibitory activity of the $CaMoO_4$/$CaSiO_3$/g-$C_3N_4$ nanocomposite against HepG-2 cells, according to certain embodiments.

DETAILED DESCRIPTION

Embodiments of the present invention will now be described more fully hereinafter with reference to the accompanying drawings wherever applicable, in that some, but not all, embodiments of the disclosure are shown.

When describing the present disclosure, the terms used are to be construed in accordance with the following definitions, unless a context dictates otherwise.

In the drawings, like reference numerals designate identical or corresponding parts throughout the several views. Further, as used herein, the words 'a', 'an', and the like generally carry a meaning of 'one or more', unless stated otherwise.

Furthermore, the terms 'approximately', 'approximate', 'about', and similar terms generally refer to ranges that include the identified value within a margin of 20%, 10%, or preferably 5%, and any values therebetween.

When amounts, concentrations, dimensions and other parameters are expressed in the form of a range, a preferable range, an upper limit value, a lower limit value or preferable upper and limit values, it should be understood that any ranges obtainable by combining any upper limit or preferable value with any lower limit or preferable value are also specifically disclosed, irrespective of whether the obtained ranges are clearly mentioned in the context.

A weight percent of a component, unless specifically stated to the contrary, is based on the total weight of the formulation or composition in which the component is included. For example, if a particular element or component in a composition or article is said to have 5 weight percentage (wt. %), it is understood that this percentage is in relation to a total compositional percentage of 100%.

The present disclosure is intended to include all hydration states of a given compound or formula, unless otherwise noted or when heating a material.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium, and isotopes of carbon include $^{13}C$ and $^{14}C$. Isotopes of oxygen include $^{16}O$, $^{17}O$, and $^{18}O$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

As used herein, the term 'porosity' refers to a measure of the void or vacant spaces within a material.

As used herein, the term 'pore diameter' refers to an average width or size of the pores (void spaces) within a material, typically measured in nm or angstroms (Å). It is a key parameter in characterizing the texture and permeability of porous materials, influencing their adsorption, filtration, or catalytic properties. The pore diameter is often determined using methods such as nitrogen adsorption or mercury intrusion, which provide insights into the material's ability to absorb or interact with molecules of specific sizes.

As used herein, the term 'pore volume' refers to the total volume of void spaces (pores) within a material that is capable of being filled by a gas or liquid.

As used herein, the term 'pharmaceutical composition' refers to a mixture of the compounds described herein or pharmaceutically acceptable salts, esters, or prodrugs thereof, with other chemical components, such as physiologically acceptable carriers and excipients.

As used herein, the term 'cancer' refers to all types of cancer, neoplasm, or malignant tumors found in mammals (e.g., humans), including leukemias, lymphomas, carcinomas, and sarcomas. Exemplary cancers that may be treated with a nanocomposite material or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the term "subject" and "patient" are used interchangeably. As used herein, they refer to any subject for whom or which therapy, including with the compositions according to the present disclosure, is desired. In most embodiments, the subject is a mammal, including but not limited to a human, a non-human primate such as a chimpanzee, a domestic livestock such as cattle, a horse, a swine, a pet animal such as a dog, a cat, and a rabbit, and a laboratory subject such as a rodent, e.g. a rat, a mouse, and a guinea pig. In preferred embodiments, the subject is a human.

The terms "administer", "administering", "administration", and the like, as used herein, refer to the methods that may be used to enable the delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), and topical and rectal administration. Those of ordinary skill in the art are familiar with administration techniques that can be employed with the compounds and methods described herein.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such teens may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with, a pathology related to or caused in part by unregulated or aberrant cellular division, (4) an increase: in disease-free, relapse-free, progression-free, and/or overall survival, duration, or rate (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

According to one aspect of the present disclosure, a method of treating cancer cells is described. The cancer cells are of a cancer selected from breast cancers and liver cancers. In a specific embodiment, the cancer cells are of estrogen receptor-positive breast cancer. In another specific embodiment, the cancer cells are of human breast carcinoma. In another specific embodiment, the cancer cells are of a cancer from hepatocellular carcinoma (HCC), cholangiocarcinoma, angiosarcoma, or fibrolamellar hepatocellular carcinoma. In one specific embodiment, the cancer cells are cancer of human HCC. The method includes incubating the cancer cells with a particulate crystalline nanocomposite in an amount sufficient to induce apoptosis or kill at least 60% of the cancer cells.

A particulate crystalline nanocomposite material is described. The particulate crystalline nanocomposite includes a tetragonal $CaMoO_4$ crystalline phase, a $CaSiO_3$ crystalline phase, and a graphitic-$C_3N_4$ crystalline phase. In some embodiments, the particulate crystalline nanocomposite may include crystalline phases, but is not limited to quartz, calcite, hematite, magnetite, goethite, dolomite, albite, anorthite, pyrite, fluorite, halite, barite, apatite, rutile, and zircon. In a preferred embodiment, the particulate crystalline nanocomposite includes crystalline phases.

In some embodiments, the ratio by weight of $CaMoO_4$ to $CaSiO_3$ to graphitic-$C_3N_4$ in the particulate crystalline nanocomposite ranges from (0.8-1.2):(0.8-1.2):(0.8-1.2), preferably (0.9-1.2):(0.9-1.2):(0.9-1.2), preferably (1.0-1.2):(1.0-1.2):(1.0-1.2), preferably (1.1-1.2):(1.1-1.2):(1.1-1.2). In a preferred embodiment, the ratio by weight of $CaMoO_4$ to $CaSiO_3$ to graphitic-$C_3N_4$ in the particulate crystalline nanocomposite is 1 to 1 to 1.

In some embodiments, the particulate crystalline nanocomposite consists essentially of sheet morphologies, preferably nanosheets, although other morphologies such as nanowires, nanospheres, nanocrystals, nanorectangles, nanotriangles, nanopentagons, nanohexagons, nanoprisms, nanodisks, nanocubes, nanoribbons, nanoblocks, nanotoroids, nanodiscs, nanobarrels, nanogranules, nanowhiskers, nanoflakes, nanofoils, nanopowders, nanoboxes, nanobeads, nanobelts, nano-urchins, nanoflowers, nanostars, tetrapods, and their mixtures thereof are also possible. In a preferred embodiment, the particulate crystalline nanocomposite has a two-dimensional porous structure constructed with curled and wrinkled nanosheets and platelets of the g-$C_3N_4$. In one embodiment, a fraction of the graphitic-$C_3N_4$ is in the form of mesoporous nanosheets. In some embodiments, at least 80 wt. %, preferably 82 wt. %, preferably 84 wt. %, preferably 86 wt. %, preferably 88 wt. %, preferably 90 wt. % of the graphitic-$C_3N_4$ is in the form of mesoporous nanosheets. In one embodiment, a fraction of the $CaMoO_4$ and a fraction of the $CaSiO_3$ of the particulate crystalline nanocomposite are in the form of substantially spherical particles. In some embodiments, at least 50 wt. %, preferably 52 wt. %, preferably 54 wt. %, preferably 56 wt. %, preferably 58 wt. %, preferably 50 wt. % of $CaMoO_4$ and CaSiO$_3$ of the particulate crystalline nanocomposite is in the form of substantially spherical particles.

In some embodiments, the substantially spherical particles have an average particle size ranging from about 5 to about 20 nm, preferably 7 to 20 nm, preferably 9 to 20 nm, preferably 11 to 20 nm, preferably 15 to 20 nm, preferably 17 to 20 nm, preferably 19 to 20 nm. In a preferred embodiment, the average particle size is 9.2 nm.

In some embodiments, the particulate crystalline nanocomposite is porous. A porous material is the one that forms a porous bulk solid. Pores may be micropores, mesopores, macropores, and/or a combination thereof. The pores exist in the bulk material, not necessarily in the molecular structure of the material. The term 'microporous' means that nanocomposite have pores with an average pore width (i.e. diameter) of less than 2 nm. The term 'mesoporous' means the pores of the nanocomposite have an average pore width of 2-50 nm. The term 'macroporous' means the pores of nanocomposite have an average pore width larger than 50 nm. Pore size may be determined by methods including, but not limited to, gas adsorption (e.g. N$_2$ adsorption), mercury intrusion porosimetry, and imaging techniques such as scanning electron microscopy (SEM), and X-ray computed tomography (XRCT). In a preferred embodiment, the particulate crystalline nanocomposite has a monomodal pore size distribution and the pore size is determined by Barrett-Joyner-Halenda (BJH) desorption analysis.

In some embodiments, the particulate crystalline nanocomposite has an average pore diameter ranging from about 15 to about 25 nm, preferably 15 to 20 nm, preferably 19 to 25 nm, preferably 21 to 25 nm, preferably 23 to 25 nm. In a preferred embodiment, particulate crystalline nanocomposite has an average pore diameter of 18.92 nm.

In some embodiments, the particulate crystalline nanocomposite has a Brunauer-Emmett-Teller (BET) surface area ranging from about 60 to about 100 m$^2$/g, preferably 65 to 100 m$^2$/g, preferably 70 to 100 m$^2$/g, preferably 75 to 100 m$^2$/g, preferably 80 to 100 m$^2$/g, preferably 70 to 90 m$^2$/g, preferably 85 to 100 m$^2$/g, preferably 90 to 100 m$^2$/g, preferably 95 to 100 m$^2$/g. The surface area is determined by Brunauer-Emmett-Teller (BET) analysis. In a preferred embodiment, the particulate crystalline nanocomposite has a BET surface area of 78.1 m$^2$/g.

In some embodiments, the particulate crystalline nanocomposite has a pore volume ranging from about 0.1 to about 0.5 cm$^3$/g, preferably 0.2 to 0.5 cm$^3$/g, preferably 0.3 to 0.5 cm$^3$/g, preferably 0.4 to 0.5 cm$^3$/g, as determined by BJH desorption analysis. In a preferred embodiment, the particulate crystalline nanocomposite has a pore volume of 0.21 cm$^3$/g.

Another aspect of the present disclosure is directed to a pharmaceutical composition, including a particulate crystalline nanocomposite and at least one pharmaceutically acceptable excipient. The particulate crystalline nanocomposite includes a tetragonal CaMoO$_4$ crystalline phase, a CaSiO$_3$ crystalline phase, and a graphitic-C$_3$N$_4$ crystalline phase, where at least a fraction of the graphitic-C$_3$N$_4$ is in the form of mesoporous nanosheets.

In some embodiments, the pharmaceutical composition, including the particulate crystalline nanocomposite, may be used in combination with one or more other antineoplastic or chemotherapeutic agents. As used herein, a "pharmaceutical composition" refers to a mixture of the active ingredient with other chemical components, such as pharmaceutically acceptable carriers and excipients. One purpose of a composition is to facilitate the administration of the crystalline nanocomposite to a subject. Pharmaceutical compositions of the present disclosure may be manufactured by processes well-known in the art, e.g., by means of conventional mixing, dissolving, granulating, dragee-making, levigating, emulsifying, encapsulating, entrapping, or lyophilizing processes. Depending on the intended mode of administration (oral, parenteral, or topical), the composition can be in the form of solid, semi-solid, or liquid dosage forms, such as tablets, suppositories, pills, capsules, powders, liquids, or suspensions, preferably in unit dosage form suitable for single administration of a precise dosage.

An anticancer agent is at least one of a mitotic inhibitor; an alkylating agent; an antimetabolite; a cell cycle inhibitor; an enzyme; a topoisomerase inhibitor; a biological response modifier, an anti-hormone; an antiangiogenic agent such as MMP-2, MMP-9 and COX-2 inhibitor; an anti-androgen; a platinum coordination complex such as, but not limited to, oxaliplatin, carboplatin; a substituted urea such as hydroxyurea; a methylhydrazine derivative; an adrenocortical suppressant, e.g., mitotane, aminoglutethimide; a hormone and/or hormone antagonist such as the adrenocorticosteriods prednisone), progestins (e.g., hydroxyprogesterone caproate), an estrogen (e.g., diethyl-stilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; anti-microtubule agents including etoposide, vinblastine, vincristine, teniposide, docetaxel, paclitaxel, vinorelbine, vindesine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer. Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate. Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included. Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 34(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltriniethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration, e.g., oral, parental, or topical, the pharmaceutical composition may be in the form of solid dosage forms such as tablets, caplets, capsules, powders, and granules, semi-solid dosage forms such as ointments, creams, lotions, gels, pastes, and suppositories, liquid dosage forms such as solutions and dispersions, inhalation dosage forms such as aerosols and sprays, or transdermal dosage forms such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of the active compounds in hydroxypropyl methyl cellulose. In the case of capsules, tablets, and pills, the dosage forms can also comprise buffering ingredients such as sodium citrate, magnesium or calcium carbonate, or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules with one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any bland fixed oil can be employed, including synthetic mono- or di-glycerides. In addition, fatty acids, such as oleic acid, find use in the preparation of injectables. Dimethyl acetamide, surfactants including ionic and non-ionic detergents, and polyethylene glycols can be used. Mixtures of solvents and wetting ingredients, such as those discussed above, are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs includes but not limited to dosage amount, treatment duration and administration methods [See: Hoover, J. E. *Remington's pharmaceutical sciences*, Mack Publishing Co., Easton, Pa., 1975; Liberman, H. A.; Lachman, L., Eds. *Pharmaceutical dosage forms*, Marcel Decker, New York, N.Y., 1980, incorporated herein by reference in their entirety]. The dosage amount and treatment duration with the pharmaceutical composition are dependent on factors such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", "pharmaceutically effective amount", or "sufficient amount" refer to the amount of the active ingredient being administered, which will relieve to some extent one or more of the symptoms of the disease being treated. The result may be a reduction and/or alleviation of the signs, symptoms, or causes of a disease or any other desired alteration of a biological system. An appropriate "effective amount" may differ from one individual to another. An appropriate "effective amount" in any individual case may be determined using techniques, such as a dose escalation study.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be before or after the composition is administered.

A treatment method may comprise administering a pharmaceutical composition of the current disclosure as a single dose or multiple individual divided doses. In some embodiments, the pharmaceutical composition is administered at various dosages (e.g. a first dose with an effective amount of 200 mg/kg and a second dose with an effective amount of 50 mg/kg). In some embodiments, the interval of time between the administration of the pharmaceutical composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the pharmaceutical composition is administered once daily for at least 2 days, 5 days, 6 days, or 7 days. In certain embodiments, the composition and one or more additional therapies are administered in less than 1 day, 1 week, 2 weeks, 3 weeks, 4 weeks, 1 month, 2 months, 3 months, 6 months, 1 year, 2 years, or 5 years apart.

EXAMPLES

The following examples demonstrate a method of treating cancer. The examples are provided solely for illustration and are not to be construed as limitations of the present disclosure, as many variations thereof are possible without departing from the spirit and scope of the present disclosure.

Example 1: Fabricating $CaSiO_3$

Equal moles of calcium nitrate and sodium metasilicate were dispersed in 100 ml of ethanol:water (1:1) in a 150 mL glass beaker and sonicated for 15 min. The mixture was transferred to a 200 mL autoclave and then placed in an oven operated at 180° C. for 2.0 h. The product was dispersed in 500 mL of distilled water with an ultrasonic bath for 10 minutes, filtered via a Buchner system, rinsed with distilled water, and dried at 120° C. for 1.0 h.

Example 2: Fabricating $g\text{-}C_3N_4$

About 30.0 g of urea was placed in a 250 mL porcelain crucible, covered with its porcelain cover, then the hall crucible and cover were raped with three layers of aluminum foil to reduce the urea loss of evaporation. The crucible was heated via a furnace set at 600° C. for 45 min.

Example 3: Fabricating the $MoO_3$

About 10.0 ammonium molybdate and 10.0 g of xylose were placed in a 500 ml beaker. 100 ml distilled water was added to the mixture and heated till a clear solution was obtained. 10 mL of concentrated nitric acid was added to the mixture, which was then heated till the carbonization of xylose. The mixture was placed in an oven set at 120° C. for 3.0 h; the black product was milled in a mortar, placed in a 150 mL porcelain dish, and calcined at 550° C. for 4.0 h.

Example 4: Fabricating the $CaMoO_4@CaSiO_3@g\text{-}C_3N_4$

An equal amount of $CaSiO_3$, $g\text{-}C_3N_4$, and $MoO_3$ was transferred to a mono wave-200 vial (G30) and dispersed in 20 mL ethylene glycol monomethyl ether via an ultrasonic bath for 30 minutes. The vial was closed with its Teflon cover and placed in the Anton-Baar Monowave-200, operated at 180° C. and 5.0 bar pressure for one hour. The product was dispersed in 1L distilled water with an ultrasonic bath for 30 minutes, filtered via a Buchner system, rinsed with distilled water, and dried at 150° C. for 2.0 h.

Example 5: Anticancer Activity

Cell line Propagation: The cells were grown on RPMI-1640 medium supplemented with 10% inactivated fetal calf serum and 50 μg/ml gentamycin. The cells were maintained at 37° C. in a humidified atmosphere with 5% $CO_2$ and were sub-cultured two to three times a week.

Example 5: Cytotoxicity Evaluation Using Viability Assay

For antitumor assays, the tumor cell lines were suspended in a medium at concentration $5\times10^4$ cell/well in Corning 96-well tissue culture plates, then incubated for 24 hr. The tested compounds were then added into 96-well plates (three replicates) to achieve ten concentrations for each compound. Six vehicle controls with media were run for each 96-well plate as a control. After incubating for 24 h, the numbers of viable cells were determined by the MTT test. Briefly, the media was removed from the 96 well plates and replaced with 100 μl of fresh culture RPMI 1640 medium without phenol red, then 10 μl of the 12 mM MTT stock solution (5 mg of MTT in 1 mL of PBS) to each well including the untreated controls. The 96-well plates were incubated at 37° C. and 5% $CO_2$ for 4 hours. An 85 μl aliquot of the media was removed from the wells, and 50 μl of DMSO was added to each well, mixed thoroughly with the pipette, and then incubated at 37° C. for 10 min. Then after, the optical density was measured at 590 nm with the microplate reader (Sunrise, TECAN, Inc, USA) to determine the number of viable cells. The percentage of viability was calculated as $[(ODt/ODc)]\times100\%$ where ODt is the mean optical density of wells treated with the tested sample. Odc is the mean optical density of untreated cells. The relation between surviving cells and drug concentration is plotted to get the survival curve of each tumor cell line after treatment with the specified compound. The 50% inhibitory concentration ($IC_{50}$) required to cause toxic effects in 50% of intact cells was estimated from graphic plots of the dose-response curve for each concentration using GraphPad Prism software (San Diego, CA).

The crystallinity and phases identification present in $CaMoO_4$/$CaSiO_3$/g-$C_3N_4$ catalyst was analyzed by powder XRD and the results are given in FIG. 1. The intense peaks and high intensity values indicate that the powder is highly crystalline. Examination of the diffraction patterns with the standard JCPDS cards reveals the presence of $CaMoO_4$ as a major and predominant phase, together with $CaSiO_3$ and g-$C_3N_4$ as minor phases. The diffraction lines at 2θ values of 18.6, 28.6, 31.2, 34.3, and 47.10 were successfully indexed to tetragonal $CaMoO_4$ (JCPDS card, No. 00-029-0351). These diffractions are, respectively assigned to (101), (112), (004), (200), and (204) plans. While the diffraction observed at 2θ values of 17.8, 30.7, and 34.10 were assigned to the anorthic phase of $CaSiO_3$ (JCPDS card, No. 01-072-1396). These diffractions were respectively coming from (111), (030), and (212) plans. The diffractions related to g-$C_3N_4$ was observed at 2θ values of 46.8, and 59.50 (COD No. 00-050-1512). Minor traces of $SiO_2$ were detected at 2θ value of 19.3 and 25.10 (Reference code No. 00-049-0629). All of these results confirmed the successful fabrication of $CaMoO_4$/$CaSiO_3$/g-$C_3N_4$.

TEM images of $CaMoO4$/$CaSiO_3$/g-C3N4 nanocomposite were presented in FIG. 2. The TEM images showed that two-dimensional porous structure constructed with curled and wrinkled nanosheets and platelets of the g-$C_3N_4$ (FIG. 2A and FIG. 2B). The image shows also well dispersion of homogeneous spherical metal oxides nanoparticles with size 9.2 nm on nanosheets of g-$C_3N_4$. The corresponding SAED pattern reveals diffraction spots with interplanar spacing of 0.42 nm, 0.27 nm, and 0.206 nm, 0.179, and 0.144 nm due to ($CaSiO_3$; 120, $CaMoO_4$: 101), ($CaMoO_4$: 200, $CaSiO_3$: 122, g-$C_3N_4$; 200) and ($CaMoO_4$: 213, $CaSiO_3$: 013), ($CaMoO_4$: 220, $CaSiO_3$: 250), ($CaMoO_4$: 321, $CaSiO_3$: 330) diffraction planes (FIG. 2F). The corresponding HRTEM of the composite shows a plane spacing of 0.31 nm related to the ($CaMoO_4$: 112, g-$C_3N_4$; 110), where 0.135 nm, and 0.128 nm related respectively to the ($CaMoO_4$: 112, g-$C_3N_4$; 221, $CaMoO_4$: 323), and ($CaMoO_4$: 400), planes, characterizing the heterostructure formation (FIG. 2C). The FFT and IFFT measurements show a d value of 0.12 nm given to $CaMoO_4$/$CaSiO_3$/g-C3N4 nanocomposite, signifying the lattice spacing of ($CaMoO_4$: 332, g-$C_3N_4$; 410) indicating the development of g-$C_3N_4$ structure (FIG. 2D and FIG. 2E).

FIG. 3A displays the nitrogen adsorption-desorption isotherms of $CaMoO_4$/$CaSiO_3$/g-$C_3N_4$ nanocomposite. The nitrogen sorption isotherm of the composite is belonging to type IV with noticed hysteresis loop, indicating the formation of mesoporous structures. However, shifting the loop to a relatively higher pressure (P/P0=0.63-1) indicates the presence of wide mesopores, which may result from the deposition of metal oxides particles in the wide pores of g-C3N4. Furthermore, the BET surface area of the $CaMoO_4$/$CaSiO_3$/g-$C_3N_4$ sample was calculated to be 78.1 $m^2$ $g^{-1}$. The marked high specific surface area reflects the good dispersion of these metal oxides nanoparticles on g-$C_3N_4$. and $CaSiO_3$. Moreover, the pore size distribution curves, plotted using the BJH method, for the $CaMoO_4$/$CaSiO_3$/g-$C_3N_4$ sample exhibited unimodal distribution with average pore diameters maximized at 18.92 nm and pore volume of 0.21 $cm^3$ $g^{-1}$. All the isotherms belong to the category H3 type of pores, which do not exhibit limiting adsorption at high P/Po and arise due to aggregation of plate-like particles giving rise to slit-shaped pores. This indicates that the assembly of $CaMoO_4$/$CaSiO_3$/g-$C_3N_4$ composite provoked a mesoporous array (FIG. 3B).

An in-vitro investigation was conducted for the $CaMoO_4$/$CaSiO_3$/g-$C_3N_4$ against the human hepatocellular carcinoma (HepG-2) and human breast carcinoma cell lines (MCF-7). A concentration range of 3.0 to 500 µg/ml $CaMoO_4$/$CaSiO_3$/g-$C_3N_4$ and the obtained results against the MCF-7 cell line is illustrated in FIG. 4. The MCF-7 cell's viability started declining with only 15.6 µg/ml $CaMoO_4$/$CaSiO_3$/g-$C_3N_4$ dose, the $IC_{50}$ was 157.7 µg/ml, and the maximum dose (500 µg/ml) showed about 86.0% inhibition of the MCF-7. Furthermore, the exact concentration range of 3.0 to 500 µg/ml $CaMoO_4$/$CaSiO_3$/g-$C_3N_4$ was applied against the HepG-2 cell line, and the obtained results are illustrated in FIG. 5. The HepG-2 cell's viability started declining with only 62.5 µg/ml $CaMoO_4$/$CaSiO_3$/g-$C_3N_4$ dose. The $IC_{50}$ was 368.8 ng/ml, and the maximum dose (500 µg/ml) showed a 65% inhibition of the HepG-2.

Numerous modifications and variations of the present disclosure are possible in light of the above teachings. It is, therefore, to be understood that within the scope of the appended claims, the invention may be practiced otherwise than as specifically described herein.

The invention claimed is:

1. A method of treating cancer cells, comprising:

incubating a plurality of cancer cells with a particulate crystalline nanocomposite, in an amount sufficient to induce apoptosis or kill at least 60% of the cancer cells, wherein the particulate crystalline nanocomposite comprises:

a tetragonal $CaMoO_4$ crystalline phase;

a $CaSiO_3$ crystalline phase; and a graphitic-C3N4 crystalline phase, wherein at least a portion of the graphitic-$C_3N_4$ is in the form of mesoporous nanosheets, wherein the cancer cells are breast cancer cells or liver cancer cells, wherein a ratio by weight of $CaMoO_4$ to $CaSiO_3$ to graphitic-$C_3N_4$ in the particulate crystalline nanocomposite is about (0.8-1.2):(0.8-1.2):(0.8-1.2), wherein at least a portion of the $CaMoO_4$ and at least a portion of the $CaSiO_3$ of the particulate crystalline nanocomposite are in the form of substantially spherical particles, and wherein the substantially spherical particles have an average particle size of about 5 to about 20 nm, wherein the particulate crystalline nanocomposite has a monomodal pore size distribution, as determined by Barrett-Joyner-Halenda (BJH) desorption analysis, wherein the particulate crystalline nanocomposite has an average pore diameter of from about 15 to about 25 nm, as determined by BJH desorption analysis, and wherein the particulate crystalline nanocomposite has a Brunauer-Emmett-Teller (BET) surface area of from about 60 to about 100 $m^2$/g.

2. The method according to claim 1, wherein:

at least 50 wt. % of the $CaMoO_4$ is in the form of substantially spherical particles, based on a total weight of the $CaMoO_4$, and at least 50 wt. % of the $CaSiO_3$ is in the form of substantially spherical particles, based on a total weight of the $CaSiO_3$.

3. The method according to claim 1, wherein at least 50 wt. % of the graphitic-$C_3N_4$ is in the form of mesoporous nanosheets, based on a total weight of the graphitic-$C_3N_4$.

4. The method according to claim 3, wherein at least 80 wt. % of the graphitic-$C_3N_4$ is in the form of mesoporous nanosheets, based on a total weight of the graphitic-$C_3N_4$.

5. The method according to claim 1, wherein the particulate crystalline nanocomposite has an average pore diameter of from about 15 to about 20 nm, as determined by BJH desorption analysis.

6. The method according to claim 1, wherein the particulate crystalline nanocomposite has a BET surface area of from about 70 to about 90 $m^2/g$.

7. The method according to claim 1, wherein the particulate crystalline nanocomposite has a pore volume of from about 0.1 to about 0.5 $cm^3/g$.

8. The method according to claim 7, wherein the particulate crystalline nanocomposite has a pore volume of from about 0.1 to about 0.3 $cm^3/g$.

9. The method according to claim 1, wherein the cancer cells are of estrogen receptor positive breast cancer.

10. The method according to claim 1, wherein the cancer cells are of human breast carcinoma.

11. The method according to claim 1, wherein the cancer cells are obtained from a cancer selected from the group consisting of hepatocellular carcinoma (HCC), cholangiocarcinoma, angiosarcoma, and fibrolamellar hepatocellular carcinoma.

12. The method according to claim 11, wherein the cancer cells are from a Human Hepatocellular Carcinoma.

13. A pharmaceutical composition comprising at least one pharmaceutically acceptable excipient and a particulate crystalline nanocomposite comprising:
   a tetragonal $CaMoO_4$ crystalline phase;
   a $CaSiO_3$ crystalline phase; and
   a graphitic-$C_3N_4$ crystalline phase having at least a portion in the form of mesoporous nanosheets.

14. The method according to claim 1, wherein a ratio by weight of $CaMoO_4$ to $CaSiO_3$ to graphitic-$C_3N_4$ in the particulate crystalline nanocomposite is about 1:1:1.

15. The method according to claim 1, wherein the substantially spherical particles have an average particle size of about 7 to about 12 nm.

16. The method according to claim 5, wherein the particulate crystalline nanocomposite has an average pore diameter of about 18.92 nm, as determined by BJH desorption analysis.

17. The method according to claim 6, wherein the particulate crystalline nanocomposite has a BET surface area of about 78.1 $m^2/g$.

* * * * *